(12) United States Patent
Itu et al.

(10) Patent No.: US 11,191,490 B2
(45) Date of Patent: Dec. 7, 2021

(54) PERSONALIZED ASSESSMENT OF PATIENTS WITH ACUTE CORONARY SYNDROME

(71) Applicant: Siemens Healthcare GmbH, Erlangen (DE)

(72) Inventors: Lucian Mihai Itu, Brasov (RO); Tiziano Passerini, Plainsboro, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 364 days.

(21) Appl. No.: 15/771,676

(22) PCT Filed: Nov. 30, 2016

(86) PCT No.: PCT/EP2016/079313
§ 371 (c)(1),
(2) Date: Apr. 27, 2018

(87) PCT Pub. No.: WO2017/093337
PCT Pub. Date: Jun. 8, 2017

(65) Prior Publication Data
US 2018/0310888 A1    Nov. 1, 2018

Related U.S. Application Data

(60) Provisional application No. 62/262,310, filed on Dec. 2, 2015.

(51) Int. Cl.
*A61B 5/00* (2006.01)
*A61B 5/02* (2006.01)
(Continued)

(52) U.S. Cl.
CPC .......... *A61B 5/7267* (2013.01); *A61B 5/0044* (2013.01); *A61B 5/02007* (2013.01);
(Continued)

(58) Field of Classification Search
CPC . G06T 2207/20081; G06T 2207/30048; G06T 2207/30104; G06T 2211/404;
(Continued)

(56) References Cited

U.S. PATENT DOCUMENTS

| 9,349,178 B1 | 5/2016 | Itu et al. | |
| 2011/0144914 A1* | 6/2011 | Harrington | .......... C12Q 1/6883 702/19 |

(Continued)

OTHER PUBLICATIONS

International Search Report dated Mar. 2, 2017 in corresponding International Application No. PCT/EP2016/079313.
(Continued)

*Primary Examiner* — Pascal M Bui Pho
*Assistant Examiner* — Alexei Bykhovski

(57) ABSTRACT

A computer-implemented method for personalized assessment of patients with acute coronary syndrome (ACS) includes extracting (i) patient-specific coronary geometry data from one or more medical images of a patient; (ii) a plurality of features of a patient-specific coronary arterial tree based on the patient-specific coronary geometry data; and (iii) a plurality of ACS-related features from additional patient measurement data. A surrogate model is used to predict patient-specific hemodynamic measures of interest related to ACS based on the plurality of features of the patient-specific coronary arterial tree and the plurality of ACS-related features from the additional patient measurement data.

21 Claims, 8 Drawing Sheets

(51) Int. Cl.

| | |
|---|---|
| *G16H 50/20* | (2018.01) |
| *G16H 50/30* | (2018.01) |
| *G16H 50/50* | (2018.01) |
| *G06T 7/00* | (2017.01) |
| *G16H 30/40* | (2018.01) |
| *A61B 6/00* | (2006.01) |
| *A61B 5/026* | (2006.01) |
| *G16H 10/60* | (2018.01) |

(52) U.S. Cl.
CPC ........ *A61B 5/02028* (2013.01); *A61B 5/7264* (2013.01); *G06T 7/0012* (2013.01); *G16H 30/40* (2018.01); *G16H 50/20* (2018.01); *G16H 50/30* (2018.01); *G16H 50/50* (2018.01); *A61B 5/026* (2013.01); *A61B 5/7275* (2013.01); *A61B 6/507* (2013.01); *A61B 2576/023* (2013.01); *G06T 2207/20081* (2013.01); *G06T 2207/30048* (2013.01); *G06T 2207/30104* (2013.01); *G06T 2211/404* (2013.01); *G16H 10/60* (2018.01)

(58) Field of Classification Search
CPC ...... G06T 7/0012; G16H 10/60; G16H 30/40; G16H 50/20; G16H 50/30; G16H 50/50; A61B 2576/023; A61B 5/0044; A61B 5/02007; A61B 5/02028; A61B 5/026; A61B 5/7264; A61B 5/7267; A61B 5/7275; A61B 6/507
See application file for complete search history.

(56) References Cited

U.S. PATENT DOCUMENTS

| | | | | |
|---|---|---|---|---|
| 2012/0072190 | A1* | 3/2012 | Sharma | G06T 7/0016 703/2 |
| 2013/0060133 | A1* | 3/2013 | Kassab | A61B 6/5217 600/431 |
| 2013/0132054 | A1 | 5/2013 | Sharma et al. | |
| 2014/0058715 | A1 | 2/2014 | Sharma et al. | |
| 2014/0379269 | A1* | 12/2014 | Schmitt | A61B 5/6852 702/19 |
| 2015/0038860 | A1 | 2/2015 | Fonte et al. | |
| 2015/0066818 | A1 | 3/2015 | Choi et al. | |
| 2015/0112182 | A1 | 4/2015 | Sharma et al. | |
| 2015/0164452 | A1 | 6/2015 | Choi et al. | |
| 2015/0245775 | A1 | 9/2015 | Fonte et al. | |
| 2016/0063175 | A1* | 3/2016 | Choi | G16B 5/00 703/11 |
| 2017/0032097 | A1 | 2/2017 | Itu et al. | |
| 2017/0245821 | A1 | 8/2017 | Itu et al. | |

OTHER PUBLICATIONS

[Rubin, J et al., 2011] Association between high-sensitivity C-reactive protein and coronary plaque subtypes assessed by 64-slice coronary computed tomography angiography in an asymptomatic population. Circ Cardiovasc Imaging. 2011.
[Samady et al., 2006] Samady H, Lepper W, Powers ER, Wei K, Ragosta M, Bishop GG, Sarembock IJ, Gimple L, Watson DD, Beller GA, Barringhaus KG. Fractional flow reserve of infarct-related arteries identifies reversible defects on noninvasive myocardial perfusion imaging early after myocardial infarction. J Am Coll Cardiol. 2006; 47(11): 2187-2193.
[Sekercioglu et al., 2014] Sekercioglu N., Spencer F.A., Lopes L.C., Guyatt G.H, Culprit vessel versus immediate complete revascularization in patients with ST-segment myocardial infarction—a systematic review, Clin Cardiol. Dec. 2014;37(12):765-72.
[Sels et al., 2011] Seis JW, Tonino PA, Siebert U, Fearon WF, Van't Veer M, De Bruyne B, Pijls NH. Fractional flow reserve in unstable angina and non-ST-segment elevation myocardial infarction experience from the FAME (Fractional flow reserve versus Angiography for Multivessel Evaluation) study. JACC Cardiovasc Interv. 2011; 4(11): 1183-1189.
[Shah et al., 2014] Nikunj R. Shah, Fractional flow reserve in acute coronary syndromes: A review, IJC Heart & Vasculature, vol. 5, Dec. 2014, pp. 20-25.
[Sharma et al., 2012] Sharma P, Itu L, Zheng X, Kamen A, Bernhardt D, Suciu C, Comaniciu D. A framework for personalization of coronary flow computations during rest and hyperemia. In: Engineering in Medicine and Biology Society (EMBC), 2012 Annual International Conference of the IEEE, 6665-6668, IEEE, 2012.
[Tanaka et al., 2009] Tanaka A, Imanishi T, Kitabata H, et al., Lipid-rich plaque and myocardial perfusion after successful stenting in patients with non-ST-segment elevation acute coronary syndrome: an optical coherence tomography study, Eur Heart J, 2009;30(11):1348-55.
[Taylor et al., 2013] Taylor CA, Fonte TA, Min JK. Computational fluid dynamics applied to cardiac computed tomography for non-invasive quantification of fractional flow reserve: scientific basis. J Am Coll Cardiol 61: 2233-2241, 2013.
[Toth et al., 2014] Toth G, Hamilos M, Pyxaras S, Mangiacapra F, Nelis O, De Vroey F, Di Serafino L, Muller O, Van Mieghem C, Wyffels E, Heyndrickx GR, Bartunek J, Vanderheyden M, Barbato E, Wijns W, De Bruyne B. Evolving concepts of angiogram: fractional flow reserve discordances in 4000 coronary stenoses. Eur Heart J 35: 2831-2838, 2014.
[Toutouzas et al., 2015] K. Toutouzas et al., Accurate and reproducible reconstruction of coronary arteries and endothelial shear stress calculation using 3D OCT: Comparative study to 3D IVUS and 3D QCA, Atherosclerosis 240 (2015), pp. 510-519.
[Tu et al., 2014] Tu S, Barbato E, Köszegi Z, Yang J, Sun Z, Holm NR, Tar B, Li Y, Rusinaru D, Wijns W, Reiber JH. Fractional flow reserve calculation from 3-dimensional quantitative coronary angiography and TIMI frame count: a fast computer model to quantify the functional significance of moderately obstructed coronary arteries. JACC Cardiovasc Interv 7: 768-777, 2014.
[Tu et al., 2015] Tu S, Bourantas CV, Nørgaard BL, Kassab GS, Koo BK, Reiber JH. Image-based assessment of fractional flow reserve. EuroIntervention 11: V50-V54, 2015.
[Val Martin et al., 2015] David del Val Martin, Marcelo Sanmartin Fernández, Jose Luis Zamorano Gómez, Biomarkers in acute coronary syndrome, IJC Metabolic & Endocrine vol. 8, Sep. 2015, pp. 20-23.
[Wald et al., 2013] Wald DS, et al. Randomized trial of preventive angioplasty in myocardial infarction. N Engl J Med 2013; 369:1115-23.
[Wilson et al. 1990] Wilson, R.F., Wyche, K., Christensen, B.V., Zimmer, S., Laxson, D.D., "Effects of Adenosine on Human Coronary Arterial Circulation", Circulation, vol. 82, pp. 1595-1606, 1990.
[Windecker et al., 2014] Windecker S, Kolh P, Alfonso F, Collet JP, Cremer J, Falk V, Filippatos G, Hamm C, Head SJ, Jüni P, Kappetein AP, Kastrati A, Knuuti J, Landmesser U, Laufer G, Neumann FJ, Richter DJ, Schauerte P, Uva MS, Stefanini GG, Taggart DP, Torracca L, Valgimigli M, Wijns W, Witkowski. 2014 ESC/EACTS Guidelines on myocardial revascularization. Eur Heart J 46: 517-592, 2014.
[Wood et al., 2013] Wood DA, Poulter RS, Boone R, Lim I, Bogale N, Starovoytov A, et al. TCT-628: Stability of non culprit vessel fractional flow reserve in patients with ST-segment elevation myocardial infarction. J Am Coll Cardiol. 2013; 62(18_S1): B191. doi:10.1016/j.jacc.2013.08.1376.
[Yang, DH et al., 2014] Association between C-reactive Protein and Type of Coronary Arterial Plaque in Asymptomatic Patients: Assessment with Coronary CT Angiography. Radiology. Apr. 3, 2014:130772.
[***WHO, 2015] World Health Organization. Global status report on noncommunicable disease 2010. WHO, 2011. Geneva: World Health Organization, 2015.
[Layland et al., 2015a] Layland J, Rauhalammi S, Watkins S, et al. Assessment of Fractional flow reserve in patients with recent non-ST segment myocardial infarction: A comparative study with 3

(56) References Cited

OTHER PUBLICATIONS tesla stress perfusion cardiac magnetic resonance imaging. Circulation: Cardiovascular Interventions 2015;8:epub ahead of press.
[Layland J, et al., 2013] Layland J, et al. Vasodilatory capacity of the coronary microcirculation is preserved in selected patients with non-ST-segment-elevation myocardial infarction. Circ Cardiovasc Interv 2013;6:231-6.
[Layland J, et al., 2015b] Layland J, et al. Fractional flow reserve versus angiography in guiding management to optimize outcomes in non-STsegment elevation myocardial infarction: the British Heart Foundation Famous-NSTEMI randomized trial. Eur Heart J 2015;36:100-11.
[Layland, 2015] Layland 2015, Fractional Flow Reserve In Acute Coronary Syndromes, RadcliffeCardiology.com, Sep. 2015.
[Lopez-Palop Carrillo et al., 2012] Lopez-Palop Carrillo P, Torres F, Lozano I, Frutos A, Avanzas P, Cordero A, et al. Results of fractional flow reservemeasurement to evaluate non-culprit coronary artery stenosis in patients with acute coronary syndrome. Rev Esp Cardiol 2012; 65(2):164-70.
[Maehara et al., 2002] Morphologic and angiographic features of coronary plaque rupture detected by intravascular ultrasound. J Am Coll Cardiol. Sep. 4, 2002;40(5):904-10.
[McLean et al., 2012] Anthony S McLean, Stephen J Huang, Cardiac biomarkers in the intensive care unit, Annals of Intensive Care 2012, 2:8.
[Min et al., 2012] Min JK, Leipsic J, Pencina, MJ, Berman DS, Koo BK, van Mieghem C, Erglis A, Lin FY, Dunning AM, Apruzzese P, Budoff MJ, Cole JH, Jaffer FA, Leon, MB, Malpeso J, Mancini GB, Park SJ, Schwartz RS, Shaw LJ, Mauri L. Diagnostic accuracy of fractional flow reserve from anatomic CT angiography. JAMA 308: 1237-1245, 2012.
[Mingels et al., 2012] Mingels AM, Joosen IA, Versteylen MO, Laufer EM, Winkens MH, Wildberger JE, Van Dieijen-Visser MP, Hofstra L. High-sensitivity cardiac troponin T: risk stratification tool in patients with symptoms of chest discomfort. PLoS One. 2012;7(4):e35059.
[Morris et al., 2013] Morris PD, Ryan D, Morton AC, Lycett R, Lawford PV, Hose DR, Gunn JP. Virtual fractional flow reserve from coronary angiography: modeling the significance of coronary lesions: results from the VIRTU-1 (VIRTUal Fractional Flow Reserve From Coronary Angiography) study. JACC Cardiovasc Interv 6: 149-157, 2013.
[Nishiguchi et al., 2010] Nishiguchi T, Kitabata H, Tanaka A, et al., Very late stent thrombosis after drug-eluting stent in segment with neointimal tissue coverage, JACC Cardiovasc Imaging, 2010;3(4):445-6.
[Nørgaard et al., 2014] Nørgaard BL, Leipsic J, Gaur S, Seneviratne S, Ko BS., Ito H, Jensen JM, Mauri L, De Bruyne B, Bezerra H, Osawa K, Marwan M, Naber C, Erglis A, Park SJ, Christiansen EH, Kaltoft A, Lassen JF, Bøtker HE, Achenbach S. Diagnostic performance of noninvasive fractional flow reserve derived from coronary computed tomography angiography in suspected coronary artery disease: the NXT trial (Analysis of Coronary Blood Flow Using CT Angiography: Next Steps). J Am Coll Cardiol 63: 1145-1155, 2014.
[Norja S et al., 2007] C-reactive protein in vulnerable coronary plaques. J Clin Pathol. 2007.
[Ntalianis et al., 2010] Ntalianis A, Seis JW, Davidavicius G, Tanaka N, Muller O, Trana C, Barbato E, Hamilos M, Mangiacapra F, Heyndrickx GR, Wijns W, Pijls NH, De Bruyne B. Fractional flow reserve for the assessment of nonculprit coronary artery stenoses in patients with acute myocardial infarction. JACC Cardiovasc Interv. Dec. 2010; 3 (12): 1274-1281.
[Papafaklis et al., 2014] Papafaklis MI, Muramatsu T, Ishibashi Y, Lakkas LS, Nakatani S, Bourantas CV, Ligthart J, Onuma Y, Echavarria-Pinto M., Tsirka G, Kotsia A, Nikas DN, Mogabgab O, van Geuns RJ, Naka KK, Fotiadis DI, Brilakis ES, Garcia-Garcia HM, Escaned J, Zijlstra F, Michalis LK, Serruys PW. Fast virtual functional assessment of Intermediate coronary lesions using routine angiographic data and blood flow simulation in humans: comparison with pressure wire-fractional flow reserve. EuroIntervention 10: 574-583, 2014.
[Petraco et al., 2013] Petraco R, Park JJ, Sen S, Nijjer SS, Malik IS, Echavarria-Pinto M, Asrress KN, Nam CW, Macías E, Foale RA, Sethi A, Mikhail GW, Kaprielian R, Baker CS, Lefroy D, Bellamy M, Al-Bustami M, Khan MA, Gonzalo N, Hughes AD, Francis DP, Mayet J, Di Mario C, Redwood S, Escaned J, Koo BK, Davies JE. Hybrid iFR-FFR decision-making strategy: implications for enhancing universal adoption of physiology-guided coronary revascularisation. EuroIntervention 8: 1157-1165, 2013.
[Pijls et al., 1996] Pijls NH, de Bruyne B, Peels K, van der Voort PH, Bonnier HJ, Bartunek J, Koolen JJ. Measurement of fractional flow reserve to assess the functional severity of coronary-artery stenoses. N Engl J Med 334: 1703-1708, 1996.
[Politi et al., 2010] Politi L, Sgura F, Rossi R, et al. A randomised trial of target-vessel versus multi-vessel revascularisation in ST-elevation myocardial infarction: major adverse cardiac events during long-term follow-up. Heart 2010;96:662-7.
[Renker et al., 2014], Renker M, Schoepf UJ, Wang R, Meinel FG, Rier JD, Bayer RR, Möllmann H, Hamm CW, Steinberg DH, Baumann S. Comparison of diagnostic value of a novel noninvasive coronary computed tomography angiography method versus standard coronary angiography for assessing fractional flow reserve Am J Cardiol 114: 1303-1308, 2014.
[Achenbach et al., 2010] Imaging of coronary atherosclerosis by computed tomography. European Heart Journal (2010).
[Altintas et al., 2015] S. Altintas et al., Unstable coronary plaque characteristics are associated with high-sensitivity cardiac troponin T and N-terminal Pro-Brain Natriuretic Peptide, Journal of Cardiovascular Computed Tomography, Oct. 2015.
[Amodio et al., 2010] Amodio G, Antonelli G, Di Serio F. Cardiac biomarkers in acute coronary syndromes: a review. Curr Vasc Pharmacol. May 2010;8(3):388-93.
[Bishop, 2006] Bishop CM. Pattern recognition and machine learning. New York, NY: Springer, 2006.
[Coenen et al., 2015] Coenen A, Lubbers MM, Kurata A, Kono A, Dedic A, Chelu RG, Dijkshoorn ML, Gijsen FJ, Ouhlous M, van Geuns RJM, Nieman K. Fractional flow reserve computed from noninvasive CT angiography data: diagnostic performance of an on-site clinician-operated computational fluid dynamics algorithm. Radiology 274: 674-683, 2015.
[De Bruyne et al., 2001] De Bruyne B, Pijls NH, Bartunek J, Kulecki K, Bech JW, De Winter H, Van Crombrugge P, Heyndrickx GR, Wijns W. Fractional flow reserve in patients with prior myocardial infarction. Circulation. 2001; 104 (2):157-162.
[De Bruyne et al., 2014] Bernard De Bruyne, Julien Adjedj, Fractional flow reserve in acute coronary syndromes, European Heart Journal, DOI: http://dx.doi.org/10.1093/eurheartj/ehu362, Sep. 2014.
[Di Mario et al., 2004] Di Mario C, Mara S, Flavio A, et al. Single vs multivessel treatment during primary angioplasty: results of the multicentre randomized HEpacoat for cuLPrit or multivessel stenting for Acute Myocardial Infarction (Help AMI) Study. Int J Cardiovasc Interv 2004;6:128-33.
[Dziewierz A, et al., 2010] Dziewierz A, et al. Impact of multivessel coronary artery disease and non-infarct-related artery revascularization on outcome of patients with ST-elevation myocardial infarction transferred for primary percutaneous coronary intervention (from the EUROTRANSFER Registry). Am J Cardiol 2010;106:342-7.
[Engstrøm et al., 2015] Engstrøm T. The third DANish study of optimal Acute treatment of patients with ST-segment elevation Myocardial Infarction: PRImary PCI in MULTIvessel disease. Presented at: American College of Cardiology/2 Scientific Session; Mar. 16, 2015; San Diego, CA.
[Farooq et al., 2011] Vasim Farooq; Salvatore Brugaletta; Patrick W Serruys, Contemporary and Evolving Risk Scoring Algorithms for Percutaneous Coronary Intervention, Heart. 2011;97(23):1902-1913.
[Fihn et al. 2012] 2012 ACCF/AHA/ACP/AATS/PCNA/SCAI/STS guideline for the diagnosis and management of patients with stable ischemic heart disease: a report of the American College of Cardiology Foundation/American Heart Association task force on practice guidelines, and the American College of Physicians, American

(56) References Cited

OTHER PUBLICATIONS

Association for Thoracic Surgery, Preventive Cardiovascular Nurses Association, Society for Cardiovascular Angiography and Interventions, and Society of Thoracic Surgeons. J Am Coll Cardiol 60: e44-e164, 2012.

[Gershlick et al., 2015] Gershlick AH, Khan JN, Kelly DJ, et al. Randomized trial of complete versus lesion-only revascularization in patients undergoing primary percutaneous coronary intervention for STEMI and multivessel disease. J Am Coll Cardiol. 2015; 65: 963-972.

[Hamm et al., 2011] Hamm CW, Bassand JP, Agewall S, et al., ESC Guidelines for the management of acute coronary syndromes in patients presenting without ST-segment elevation. The task force for the management of acute coronary syndromes (ACS) in patients presenting without persistent ST-segment elevation of the European Society of Cardiology (ESC), Eur Heart J, 2011;32(23):2999-3054.

[Itu et al., 2012] Itu L, Sharma P, Mihalef V, Kamen A, Suciu C, Comaniciu D. A patient-specific reduced-order model for coronary circulation. In: Biomedical Imaging (ISBI), 2012 9th IEEE International Symposium on, 832-835, IEEE, 2012.

[Kim J et al., 2013] The role of critical shear stress on acute coronary syndrome. Clin Hemorheol Microcirc. 2013.

[Koo et al., 2011] Diagnosis of ischemia-causing coronary stenoses by noninvasive fractional flow reserve computed from coronary computed tomographic angiograms: results from the prospective multicenter Discover-Flow (Diagnosis of Ischemia-Causing Stenoses Obtained Via Noninvasive Fractional Flow Reserve) study. J Am Coll Cardiol 58: 1989-1997, 2011.

[Korosoglou et al., 2011] Korosoglou G, Lehrke S, Mueller D, Hosch W, Kauczor HU, Humpert PM, Giannitsis E, Katus HA. Determinants of troponin release in patients with stable coronary artery disease: insights from CT angiography characteristics of atherosclerotic plaque. Heart. 2011;97(10):823-831.

[Kubo et al., 2011] Kubo T, Ino Y, Tanimoto T, et al.. Optical coherence tomography imaging in acute coronary syndromes, Cardiol Res Pract, 2011;2011:312978.

\* cited by examiner

PERSONALIZED ASSESSMENT OF PATIENTS WITH ACUTE CORONARY SYNDROME

CROSS-REFERENCE TO RELATED APPLICATIONS

This application claims the benefit of U.S. Provisional Application Ser. No. 62/262,310 filed Dec. 2, 2015, which is incorporated herein by reference in its entirety.

TECHNOLOGY FIELD

The present invention relates generally to methods, systems, and apparatuses for personalized assessment of patients with acute coronary syndrome (ACS). The disclosed techniques may be applied, for example, predicting hemodynamic measures of interest and the risk of future events in ACS patients.

BACKGROUND

Cardiovascular disease is the leading cause of death, globally. Of these deaths, approximately 42% are caused by Coronary Artery Disease (CAD). CAD patients suffer from a buildup of plaque in the coronary arteries, which results in a corresponding decrease of blood flow to the cardiac muscle, especially under stress. In severe cases, this reduction in flow can result in myocardial ischemia, and potentially death.

The decision to revascularize blocked coronaries is commonly performed considering anatomical markers extracted from invasive coronary angiography, such as the percentage reduction in lumen diameter. There is strong evidence that this approach has a limited accuracy in evaluating the hemodynamic significance of lesions in patients with stable angina.

In view of the limitations of the pure anatomical evaluation of CAD, for patients with stable angina the functional index of Fractional Flow Reserve (FFR) has been introduced as an alternative for evaluating the hemodynamic significance of coronary artery stenoses. FFR is defined as the ratio of flow in the stenosed branch at hyperemia—a condition of stress, with maximum coronary blood flow—to the hypothetical hyperemic flow in the same branch under healthy conditions. This can be shown to be closely approximated by the ratio of hyperemic cycle-averaged pressure distal to the stenosis to the cycle-averaged aortic pressure. In patients with stable angina, FFR is currently the gold standard for determining the functional severity of a lesion. Clinical evaluation of FFR is done under angiographic guidance, using a catheter-based pressure transducer. Despite the advantages offered by FFR, the use of FFR is still relatively uncommon due to additional costs, the need to administer drugs to induce hyperemia, and the invasive nature of the measurement.

Recently, blood flow computations performed using computational fluid dynamics (CFD) algorithms in conjunction with patient-specific anatomical models extracted from medical images (e.g., CT scans of the heart and the coronary arteries) have shown great promise in being able to predict invasive, lesion-specific FFR from patient's medical images taken at resting conditions. The CFD-based models combine geometrical information extracted from medical imaging with background knowledge on the physiology of the system, encoded in a complex mathematical fluid flow model consisting of partial differential equations which can be solved only numerically. This approach leads to a large number of algebraic equations, making it computationally very demanding. Typically the solution of the flow problem requires a few hours on powerful clusters for high-fidelity models representing the complete three-dimensional velocity field to minutes on a workstation for reduced-order models which solve for time-varying pressure and flow rate in each branch. The computationally demanding aspect of these CFD models and associated image segmentation process prevents adoption of this technology for real-time applications such as intra-operative guidance of interventions.

An alternative approach with high predictive power is based on machine learning (ML) algorithms. In this case, the relationship between input data (e.g. the anatomy of a vascular tree, and quantities of interest) is represented by a model built from a database of samples with known characteristics and outcome. Once the model is trained, its application to unseen data provides results almost instantaneously.

Acute Coronary Syndrome (ACS) refers a range of conditions associated with sudden, reduced blood flow to the heart. There are generally three categories of ACS. First, in ST-segment elevation myocardial infarction (STEMI), a thrombus fully occludes a coronary artery leading to necrosis in part of the myocardium, whose size depends on how fast blood flow is reestablished. Secondly, in Non ST-segment elevation myocardial infarction (NSTEMI), blood flow is partially blocked by a thrombus, leading to significant myocardial damage. The third category of ACS is Unstable Angina (UA), wherein blood flow is partially blocked by a thrombus with no significant myocardial damage While STEMI can quickly be diagnosed from echocardiogram (ECG) signals, it is initially difficult to distinguish between NSTEMI and UA. Typically, with NSTEMI the symptoms (e.g., chest pain, nausea, and elevated heart rate) are more severe, and a blood test performed for cardiac troponins around twelve hours after the onset of the event enables a distinction between the two types of ACS.

In patients with ACS, the culprit artery (i.e., the artery which caused the myocardial infarction/lead to a state with unstable angina) may be distinguished from non-culprit arteries (i.e., all other coronary arteries, which may or may not contain stenoses causing stable angina). Since a large percentage of ACS patients have multi-vessel disease, the number of non-culprit lesions requiring decision making may be significant. After percutaneous coronary intervention (PCI) of the culprit artery, patients with multi-vessel disease have increased one-year mortality, and overall worse outcomes.

In STEMI patients there has been a continuous debate whether to stent or not the non-culprit stenoses (the stenosis of the culprit artery is stented in almost all cases). Meta-analyses and non-randomized registry studies have indicated that if all non-culprit vessels are treated the number of adverse invents increases compared to the case when only the culprit vessel is treated. Thus, the 2013 ACC/AHA/SCAI STEMI guidelines stated that only the culprit stenosis should be stented. However, prior to the publication of these guidelines, two small scale studies have indicated that PCI of non-culprit arteries reduces the risk of MI and the need to repeat revascularization. The results of three recent larger scale studies (PRAMI, CvLPRIT and PRIMULTI) have then confirmed that better patient outcome statistics are obtained if, besides the culprit artery, all other arteries with hemodynamically significant stenoses are treated. The essential question is: how to decide if a non-culprit stenosis is hemodynamically significant? Similar to the case of stable patients, angiographic markers have a limited accuracy in ACS patients, but there has also been a continuous debate whether FFR is suitable for decision-making.

Besides angiography, two other medical imaging techniques are typically used in ACS patients: Intravascular ultrasound (IVUS) and Optical coherence tomography (OCT). IVUS was the established standard intracoronary imaging technique, but due to its significantly better resolution, OCT usage has increased over the last years and represents currently the state-of-the-art. Besides lumen assessment, OCT is employed for visualizing and assessing coronary plaque (rupture, thin cap fibroatheroma, fibrous cap thickness). OCT is now considered indispensable in ACS patients. It has been shown that disruption and inflammation of the plaque are major factors in ACS, conditions which can readily be identified through OCT. Furthermore, OCT has been employed to predict patient outcome after PCI: patients with no reflow have a higher incidence of thin cap fibroatheroma compared to patients with good reflow. OCT may further be used to assess stent thrombosis, which has been shown to cause ACS. OCT and IVUS have been furthermore used to generate more accurate 3D reconstructions of the coronary arteries by fusing 3D centerlines generated from two angiographic projections and lumen information from OCT/IVUS.

Biomarkers are also typically used in risk stratification of ACS patients. As mentioned above, a troponin test can distinguish between NSTEMI and UA. High sensitivity cardiac troponin T (hs-cTnT) assay can now be used for a more sensitive detection of low troponin concentrations. hs-cTnT has been previously correlated with vulnerable plaque: the increase in troponin concentration may be caused by small plaque ruptures, which cause micro-injury in the myocardial beds. Another biomarker, N-terminal pro-B-type natriuretic peptide (NT-proBNP), has been linked with an increased risk of a major adverse cardiac event (MACE) in patients with stable CAD. Very recently hs-cTnT and NT-proBNP have been associated with various plaque characteristics (total plaque volume, calcified volume, etc.), as extracted from computed tomography angiography (CTA) images.

Thus, clinical decision making in patients with acute coronary syndromes is challenging. As opposed to the case of stable CAD, where FFR, with a universally accepted cut-off value, is the gold standard, the diagnosis and treatment of ACS patients (especially of non-culprit lesions in ACS patients) remains controversial. Several small studies have indicated that FFR can be readily used for determining the functional significance of non-culprit lesions in STEMI patients, and both culprit and non-culprit lesions in NSTEMI and UA patients.

Computational modeling has up to date been used to estimate FFR in stable CAD patients. However, it has not been applied for ACS patients, primarily due to the large computational time which is in contradiction with the requirement of fast decision making in the clinical setting. With the introduction of machine learning based techniques, which provide results in an interactive manner, non-invasive estimations of diagnostic measures of interest may be used to improve patient stratification, and reduce costs and risks. To enable accurate estimations, however, the computational techniques (computational modeling/machine learning based) need to be adapted to the conditions of ACS.

SUMMARY

Embodiments of the present invention address and overcome one or more of the above shortcomings and drawbacks, by providing methods, systems, and apparatuses related to a personalized assessment of patients with ACS. More specifically, the techniques described herein utilize ML algorithms for predicting hemodynamic measures of interest (FFR, IFR, wall stress, etc.) in ACS patients. The prediction is based on various features extracted from non-invasive patient data, medical imaging (invasive and non-invasive, perfusion), invasive measurements, blood biomarkers, etc. Furthermore, the disclosed techniques may also be applied to the prediction of risk of future events.

According to some embodiments, a computer-implemented method for personalized assessment of patients with acute coronary syndrome (ACS) includes extracting (i) patient-specific coronary geometry data from one or more medical images of a patient; (ii) a plurality of features of a patient-specific coronary arterial tree based on the patient-specific coronary geometry data; and (iii) a plurality of ACS-related features from additional patient measurement data. The additional patient measurement data may include, for example, one or more of perfusion imaging data, invasive measurements, blood biomarkers, ECG signals, or contrast propagation information. A surrogate model is used to predict patient-specific hemodynamic measures of interest related to ACS based on the plurality of features of the patient-specific coronary arterial tree and the plurality of ACS-related features from the additional patient measurement data. These patient-specific hemodynamic measures of interest may include, for example, one or more of Fractional Flow Reserve, Coronary Flow Reserve, wall shear stress, and/or a risk of plaque rupture. In some embodiments, the method further includes predicting a risk of future events for patients with ACS based on the patient-specific hemodynamic measures of interest.

In some embodiments of the aforementioned method, the surrogate model is trained using a process comprising generating a database of coronary arterial trees representative of ACS conditions. Each coronary artery tree may be generated, for example, by specifying or adapting one or more of (i) a culprit artery; (ii) a $TCRI_{ACS}$ value; or (iii) an indication of extent of myocardial area corresponding to the coronary artery tree. Flow computations are performed on each artery included in the database of coronary arterial trees to extract hemodynamic measures of interest. Next, features of coronary arterial trees and ACS related features are extracted from the database of coronary arterial trees. Then, one or more machine learning methods are applied to train the surrogate model to predict the hemodynamic measures of interest based on the features of coronary arterial trees and the ACS related features.

The database of coronary arterial trees used for training the surrogate model may include, for example, a plurality of synthetic coronary arterial trees. In some embodiments, the database of coronary arterial trees comprises a plurality of in silico models and the flow computations performed during training comprise computational fluid dynamics (CFD) computations. In other embodiments, the database of coronary arterial trees comprises a plurality of in vitro models and the flow computations comprise flow experiments. In addition to (or as an alternative to) synthetic coronary arterial trees, the database may include non-synthetic coronary arterial trees.

In some embodiments of the method discussed above, the method further include determining a confidence interval or a measure of uncertainty for the patient-specific hemodynamic measures of interest related to ACS. For example, in one embodiment, the confidence interval or measure of uncertainty is determined by comparing the predictions of the surrogate model based on medical images of the patient-specific coronary geometry acquired with at least two different imaging modalities.

According to another aspect of the present invention, a second computer-implemented method for personalized assessment of patients with ACS includes extracting (i) patient-specific coronary geometry data from a plurality of medical images and (ii) geometric features of a patient-specific vessel tree based on the patient-specific coronary geometry data. A first machine learning algorithm is used to determine one or more patient-specific hemodynamic measures of interest under stable conditions based on the patient-specific vessel tree. Next, ACS-related features are extracted from additional patient measurement data. Then, a second machine learning algorithm is used to refine the one or more patient-specific hemodynamic measures of interest based on the plurality of ACS-related features. In some embodiments, the method further includes predicting a risk of future events for patients with ACS based on the one or more patient-specific hemodynamic measures of interest. Additionally (or alternatively), the method may include predicting the evolution in time of the hemodynamic measures of interest after onset of ACS.

According to other embodiments, a parallel processing computing system includes host computer which is configured to (i) extract patient-specific coronary geometry data from one or more medical images of a patient, (ii) extract features of a patient-specific coronary arterial tree based on the patient-specific coronary geometry data, and (iii) extract a plurality of ACS-related features from additional patient measurement data. The parallel processing computing system also includes a device computer which is configured to predict patient-specific hemodynamic measures of interest related to ACS based on the features of the patient-specific coronary arterial tree and the ACS-related features from the additional patient measurement data by applying one or more machine learning algorithms in parallel across a plurality of computation units.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to personalized assessment of patients with ACS. Briefly, invasive and/or non-invasive data of the patient is acquired. Features are extracted from the input data, which may be related to the coronary geometry or to other measures acquired from the patient. Next, hemodynamic indices of interest are predicted. An offline trained machine learning algorithm is used to predict these indices at any location of the coronary arterial tree. The training is based on computational modeling. Then, the predicted hemodynamic indices of interest for the ACS patient may be visualized.

Figure 1:
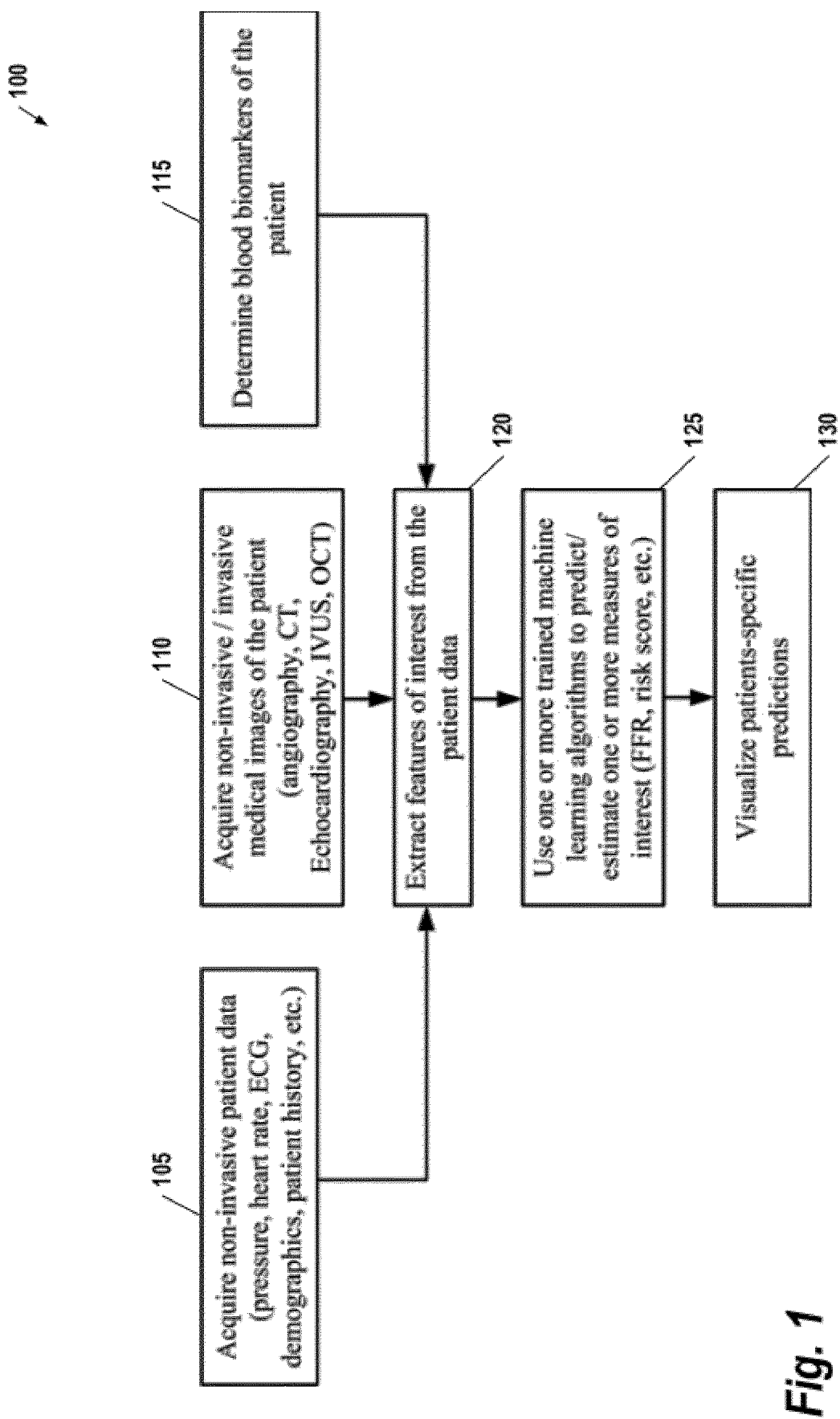
FIG. 1 illustrates a generic workflow that may be used for predicting measures of interest for patients with acute coronary syndrome, according to some embodiments.

FIG. 1 displays a generic workflow 100 that may be used for predicting measures of interest for patients with acute coronary syndrome, according to some embodiments. The central element of the workflow is represented by one or more trained ML algorithms which use a set of features for the prediction. This workflow is described below as a series of steps; however, it should be understood that order should not be implied by the description of these steps. For example, acquisition steps 105-115 could be perform in any order and multiple acquisition steps may be performed in parallel.

At step 105, non-invasive patient data is received such as, for example, blood pressure, heart rate, ECG signals, demographics, patient history, family history, etc. Non-invasive/invasive medical images of the patient are received at step 110. These images may generally be received from any source including, for example, angiography, computed tomography, echocardiography, IVUS, and OCT scanners. At step 115, blood biomarkers are received. The information acquired at steps 105-115 may be acquired at a single time point, or at different time points. For example, features extracted from a Cardiac Computed Tomography Angiography (CCTA) exam performed several months before the event of ACS and from an angiographic exam performed right after the ACS event may be used to predict the measure of interest. Similarly, blood biomarkers (the same or different) may have been acquired at different time points and used as features of the ML algorithm.

At step 120, features of interest are extracted from the patient data acquired at steps 105-115, for example, using feature extraction techniques generally known in the art. The term "extraction," as used herein refers to the act or process of retrieving data out of one or more data sources for further processing or storage. The act of extracting data may include the identification of data in a data source. For example, during extraction relevant features from an image may be identified and retrieved from the data (e.g., by cropping).

Alternatively, a feature extraction process may take such an identification as input and only perform the steps associated with retrieval.

Returning to FIG. 1, at step 125, one or more trained ML algorithms are used to predict/estimate one or more measures of interest such as FFR, risk score, etc. The one or more ML algorithms may be used in a cascaded or parallel workflow, and may be trained on patient-specific and/or on synthetic data, generated in vitro or in silico. In general, any ML algorithm known in the art may be applied including, for example, algorithms based on artificial neural networks (ANN), deep learning, or learning classifier/regression systems.

Continuing with reference to FIG. 1, at step 130, patient-specific predictions are visualized based on the output of the ML algorithms. For example, in some embodiments, the data is presented in a numeric (e.g. tabular) form to the clinician. In other embodiments, the data is presented in a graphical way (e.g., overlaid on the medical images) and presented to the clinician.

There are two general approaches for estimating the hemodynamic measures of interest in patients including, without limitation, Fractional Flow Reserve (FFR), Coronary Flow Reserve (CFR), instant wave-free ratio (iFR), Basal Stenosis Resistance (BSR), Hyperemic Stenosis Resistance (HSR), and wall shear stress (WSS). In some embodiments, the workflow can be implemented with a single ML model. In other embodiments, the workflow is implemented with cascaded ML models. Each of these implementation strategies are described below in detail.

Where a single ML model is employed, the model may be trained based on the estimations extracted from a computational model of the coronary circulation. Conventional systems for patient-specific computational modeling of the coronary circulation in stable patients rely on an anatomical model of the coronary circulation generated from medical images and on a method for personalizing the boundary conditions of the flow computation so as to match the patient-specific measurements. In the ACS setting the methodology is similar, however, due to the myocardial infarction/unstable angina, the microvasculature is affected and the capability of achieving maximal hyperemia is impaired.

A total coronary resistance index (TCRI) is typically used to describe the effect of hyperemia on the microvasculature:

$$TCRI = \frac{\frac{MAP_{hyper}}{Q_{hyper}}}{\frac{MAP_{rest}}{Q_{rest}}} = \frac{(R_{cor})_{hyper}}{(R_{cor})_{rest}} \quad (1)$$

where MAP is the mean aortic pressure, Q is the flow rate, $R_{cor}$ is the coronary microvascular resistance, and hyper and rest refer to the hyperemic/rest state of the patient. In stable patients the mean value of TCRI determined in physiological studies was of 0.22. ACS patients will typically have larger TCRI values due to the microvascular impairment. This effect will be more pronounced for the culprit arteries and in STEMI patients, and less pronounced in non-culprit arteries and NSTEMI/UA patients.

Hence, an index $TCRI_{ACS}$ may be defined. Whereas the original TCRI value is considered to be identical for all arteries, $TCRI_{ACS}$ is defined separately for each artery in the range between a minimal value corresponding to stable patients (e.g., 0.22 as indicated above) and 1.0 (hyperemic response of the myocardial bed is completely absent).

Various methods may be used to estimate $TCRI_{ACS}$ for each artery (for each outlet of the coronary anatomical model). Several methods are discussed in further detail below, including techniques that estimate $TCRI_{ACS}$ based on medical imaging techniques, blood biomarkers, contrast propagation information, invasive coronary pressure/velocity measures, and myocardial jeopardy scores. Any of these methods may be used independently or combined so as to obtain an improved estimation of the hyperemic impairment and of $TCRI_{ACS}$ respectively.

In some embodiments, medical imaging techniques are employed to estimate the perfusion of the myocardium (echocardiography with contrast agent, SPECT, PET, CT-Perfusion, etc.). Next, $TCRI_{ACS}$ is defined as a function of the distance d between the myocardial bed of the current coronary artery and the myocardial area affected by the ACS:

$$TCRI_{ACS} = f(d, TCRI) \quad (2)$$

where TCRI is the index value prior to the MI (the population average value of 0.22 may be used, or a patient-specific value determined in a previous exam either invasively or through non-invasive perfusion imaging). For example, to apply this method, first the myocardial bed corresponding to each terminal coronary artery is identified, and, then the distance may be measured between the centroid of the current myocardial bed and the centroid of the myocardial bed affected by the ACS. If perfusion imaging is not available, population average distances between myocardial beds may be employed (typically the culprit artery is identified in the cath lab during the post-MI angiographic exam).

In other embodiments, blood biomarkers may be used to estimate $TCRI_{ACS}$ as follows:

$$TCRI_{ACS} = f(cTnI, cTnT, hs\text{-}cTnT, NT\text{-}proBNP, CK, CK\text{-}MB, CHOL, CRP, etc.) \quad (3)$$

where cTnI is cardiac troponin I, cTnT is cardiac troponin T, CK is creatine kinase, and CK-MB is creatine kinase myocardial band, CHOL is total cholesterol. CRP is the level of serum C-reactive protein, which is another known prognostic factor for acute coronary events and sudden cardiac death, as well as coronary calcification. Other blood biomarkers may also be used, like: C-reactive protein, lactate dehydrogenase (LDH), aspartate transaminase (AST), myoglobin (Mb), ischemia-modified albumin (IMA), glycogen phosphorylase isoenzyme BB, high-density lipoprotein (HDL) cholesterol, low-density lipoprotein (LDL) cholesterol, pregnancy associated plasma protein A (PAPP-A), insulin-like growth factor binding protein-4 (IGFBP-4) and its fragments, myeloperoxidase (MPO), fatty acid binding protein (FABP), troponin C (TnC), D-dimer and high molecular weight fibrin degradation products, soluble CD40 ligand (sCD40L), cystatin C, human serum albumin (HSA), procalcitonin (PCT), glycogen phosphorylase isoenzyme BB (GPBB), serum amyloid A (SAA), retinol-binding protein 4 (RBP4), soluble lectin-like oxidized LDL receptor (sLOX-1), adiponectin (Adn), S100 protein. The values of these biomarkers may be used to estimate the severity of myocardial infarction, and, thus also the level of hyperemic impairment.

In other embodiments, $TCRI_{ACS}$ may be estimated using contrast propagation information. Angiographic images may be acquired at rest and at pharmacologically induced hyperemia and employed to derive surrogate measures for the rest and hyperemic coronary flow velocities ($v = d/(n \cdot \Delta t)$) where d is the distance along the centerline of the vessel, n is the number of frames required by the contrast agent to travel the distance d and Δt is the interval of time between two frames. Thus, $TCRI_{ACS}$ may be determined as follows:

$$TCRI_{ACS} = \frac{v_{hyper}}{v_{rest}} \quad (4)$$

In other embodiments, $TCRI_{ACS}$ is estimated using invasive coronary pressure and velocity measurements by combining computational modeling and invasive measurements so as to enhance the estimations output by the computational model. For example, the coronary flow velocity may be measured, and the flow rate may be derived from the volume of the reconstructed anatomical model. $TCRI_{ACS}$ may then be determined as the ratio of measured hyperemic flow rate and flow rate estimated at rest.

In other embodiments, $TCRI_{ACS}$ is estimated based on myocardial jeopardy scores. several such measures have been introduced in the past to estimate risk scores related to the myocardium based on the severity of the stenoses and on the volume of myocardium supplied by the corresponding artery. Examples of techniques that may be used for calculating $TCRI_{ACS}$ include, without limitation, duke jeopardy score, myocardial jeopardy index, and the Alberta Provincial Project for Outcome Assessment in Coronary Heart Disease (APPROACH) lesion score.

In ACS in general and STEMI in particular, a necrotic myocardial area may develop, where the oxygen demand is significantly reduced. As a result both rest and hyperemic flow rate values are reduced. After a period of time of recovery the TCRI index may recover to its original value, but both hyperemic and rest flow rates remain reduced. Several methods may be used to estimate the reduction in rest state flow rate for coronary arteries supplying partially necrotic myocardial beds. In some embodiments, a medical imaging technique is employed to estimate perfusion of the myocardium (echocardiography with contrast agent, SPECT, PET, CT-Perfusion, etc.):

$$(q_{rest})_{ACS} = r \cdot q_{rest} \quad (5)$$

where $q_{rest}$ is the rest state flow rate of the coronary artery before the ACS, $(q_{rest})_{ACS}$ is the rest state flow rate of the coronary artery after the ACS, and r is the ratio between necrotic volume and total volume of the myocardial bed supplied by the coronary artery. In other embodiments, contrast propagation information is used to derive the rest state flow rate. As described above, the coronary velocity may be estimated from the angiographic images, and then used in conjunction with the volume of the reconstructed anatomical model to derive the flow rate. In other embodiments, the reduction in rest state flow rate is estimated using features extracted from the ECG signals. The $TCRI_{ACS}$ value of the culprit artery may then be estimated with one of the methods described above.

Techniques are known in the art for training a ML model based on synthetically generated coronary geometries for predicting hemodynamic metrics of interest. For the training phase, the target values of the hemodynamic metrics of interest were generated by a computational blood flow model run on the synthetic coronary geometries. This methodology can be extended as follows for the ACS setting. First, synthetic coronary geometries are generated as described before. The parameter values used for the generation of the synthetic geometries may be adapted so as to reflect ACS patients (one culprit artery may be defined for each coronary tree with a severe stenosis or with total occlusion). Secondly, a $TCRI_{ACS}$ value may be defined for each coronary artery, e.g. based on the distance from the current artery to the culprit artery. Third, an arbitrary value of r (Equation (5)) may be used to define the extent of MI in the synthetic geometry. These parameters are used also as features during the training and prediction phase (a binary feature determining if the current artery is a culprit or a non-culprit artery, $TCRI_{ACS}$ value of each terminal artery, r value for the culprit artery).

Figure 2:
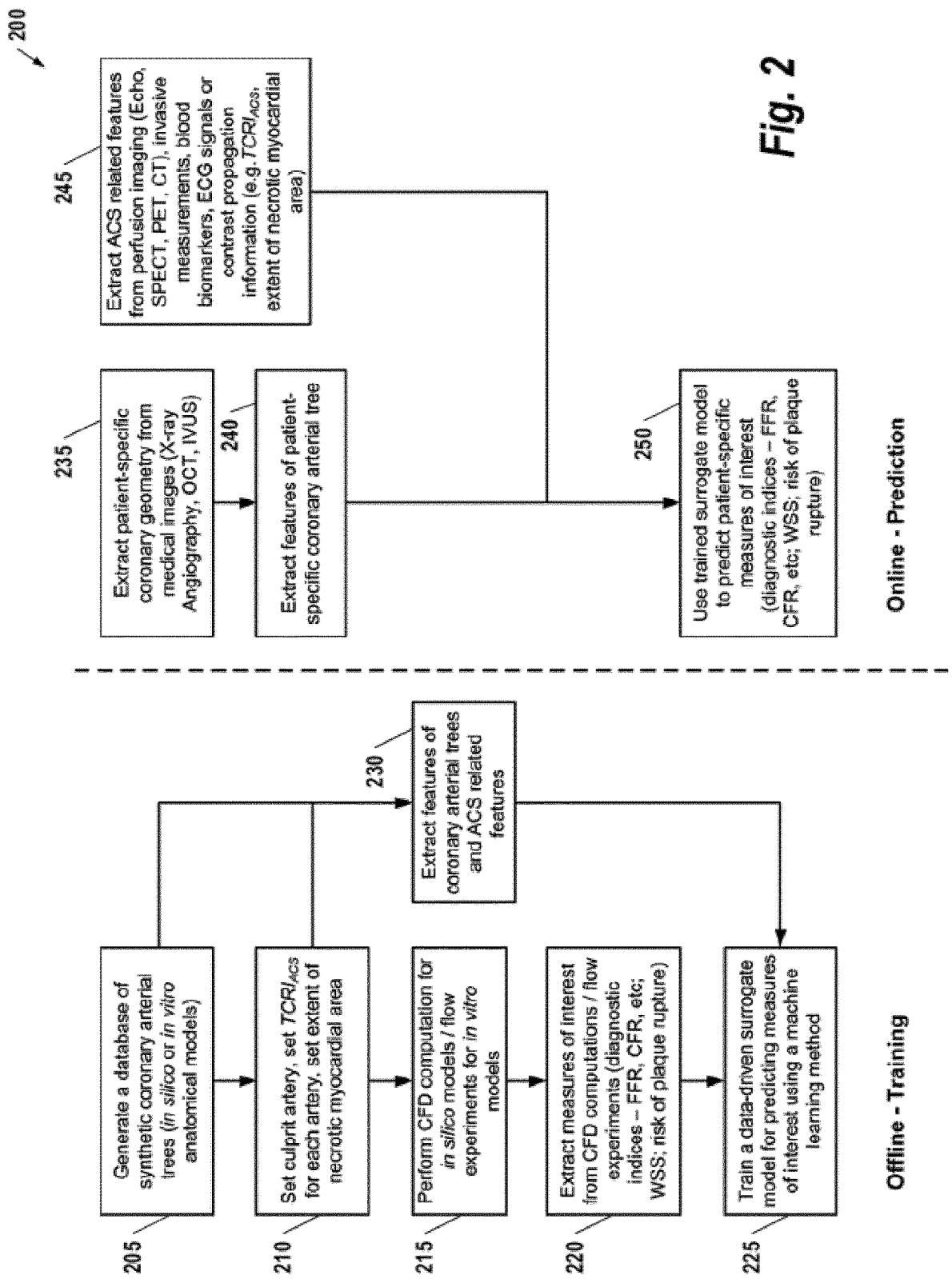
FIG. 2 shows a workflow used for the estimation of a quantity of interest in ACS patients from a single machine learning model, according to some embodiments.

FIG. 2 displays the workflow 200 of the above described methodology. The workflow 200 includes an offline training phase and an online prediction phase. During the offline training phase, a data-driven surrogate model is trained as follows. Starting at step 205 a database of synthetic coronary arterial trees is generated, for example, in silico or in vitro models. In some embodiments, if real patient data is available, it may be used to supplement or replace the synthetic data generated at step 205. Next, at step 210, the culprit artery is set and the $TCRI_{ACS}$ is set for each artery, for example, based on user input or through automatic selection techniques generally known in the art. Additionally, at step 205 the extent of necrotic myocardial area is set.

Continuing with reference to FIG. 2, CFD computation is performed at step 215 for in silico models. Alternatively (or additionally), for any in vitro models, flow experiments may be performed at 220 to evaluate flow across the artery of interest. Next, at step 220, measures of interest are extracted from the CFD computations or flow experiments. These may include, for example, diagnostic indices (FFR, CFR, etc.), WSS, or risk of plaque rupture. At step 230, performed prior to, during, or after steps 215-220, features of coronary arterial trees and ACS related features are extracted from the data provided at steps 205 and 210. Finally, at step 225, the data extracted at steps 220 and 230 is used to train a data-driven surrogate model for predicting measures of interest. The form of training will depend on the ML method being employed. For example, for a neural network, an iterative learning process may be utilized in which data cases are presented to the network one at a time, and the weights associated with the input values are adjusted each time.

Figure 3:
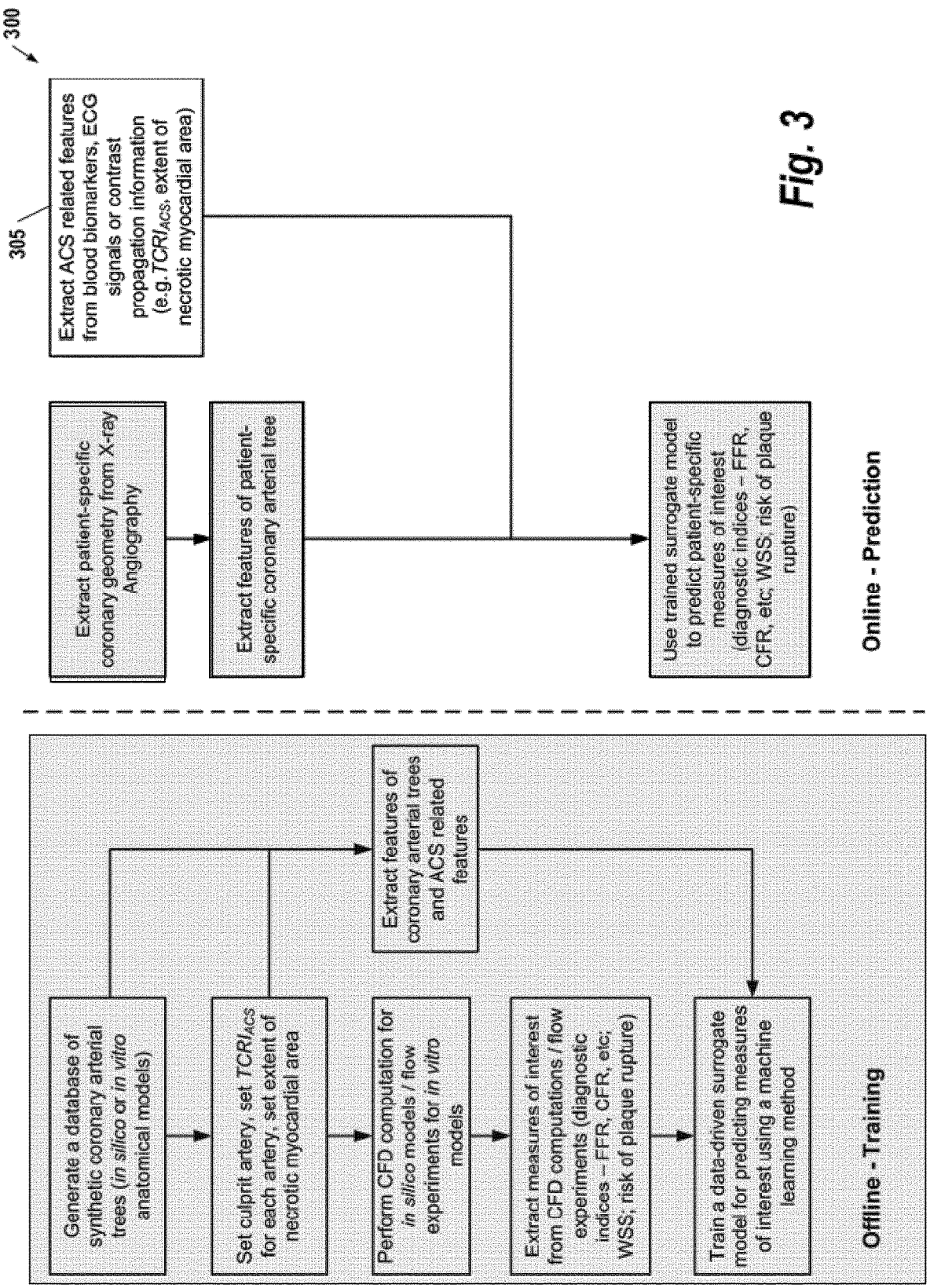
FIG. 3 shows a workflow used for the estimation of a quantity of interest in ACS patients, based on angiography blood biomarkers and ECG signals, according to some embodiments.

During online-prediction phase, at step 235, patient-specific coronary geometry is extracted from medical images (e.g., X-ray, Angiography, OCT, IVUS). A fusion of the images may be performed to provide more accurate values for the geometric features. Next, at step 240, features of a patient-specific coronary arterial tree are extracted from the image data. At step 245, ACS related features are extracted from additional data sources such as perfusion imaging (e.g., Echo, SPECT, PET, CT, etc.), invasive measurements, blood biomarkers, ECG signals, and/or contrast propagation information. At step 250, the trained surrogate model is used to predict patient-specific measures of interest such as diagnostic indices (FFR, CFR, etc.), WSS, or risk of plaque rupture Although FIG. 2 focuses on the configuration with synthetic geometries and synthetic data, patient-specific geometries and features may be used during the training phase (exclusively or alongside synthetic data). In a typical clinical setting, an ACS patient receives an angiographic exam, ECG test and a blood test for biomarkers. Hence the workflow displayed in FIG. 2 may be adapted for this use case, as displayed in the workflow 300 shown in FIG. 3. In FIG. 3, portions of the workflow 300 that are identical to the workflow 200 in FIG. 2 have been grayed out. Thus, the variation is that at step 305, all ACS related features are extracted from the contrast propagation information, blood biomarkers, or the risk scores. Some of the features used in the workflow in FIG. 2 may be estimated from the available data or from population average values including, without limitation, the distance between the myocardial bed of the current coronary artery and/or the myocardial area affected by the ACS and the ratio between necrotic volume and total volume of the myocardial bed supplied by the coronary artery.

The alternative to the approach described in the previous section is to use cascaded ML models, whereas the last ML model in the cascade predicts the measure of interest for the ACS patient. As an example, a workflow with two cascaded models may be used. The first ML model predicts the patient specific measure of interest under conditions of stable ischemia. Any of the methods described in the previous patent applications may be used. The second ML model in the workflow adapts the output of the first model so as to predict the patient specific measure of interest in the setting of ACS.

Figure 4:
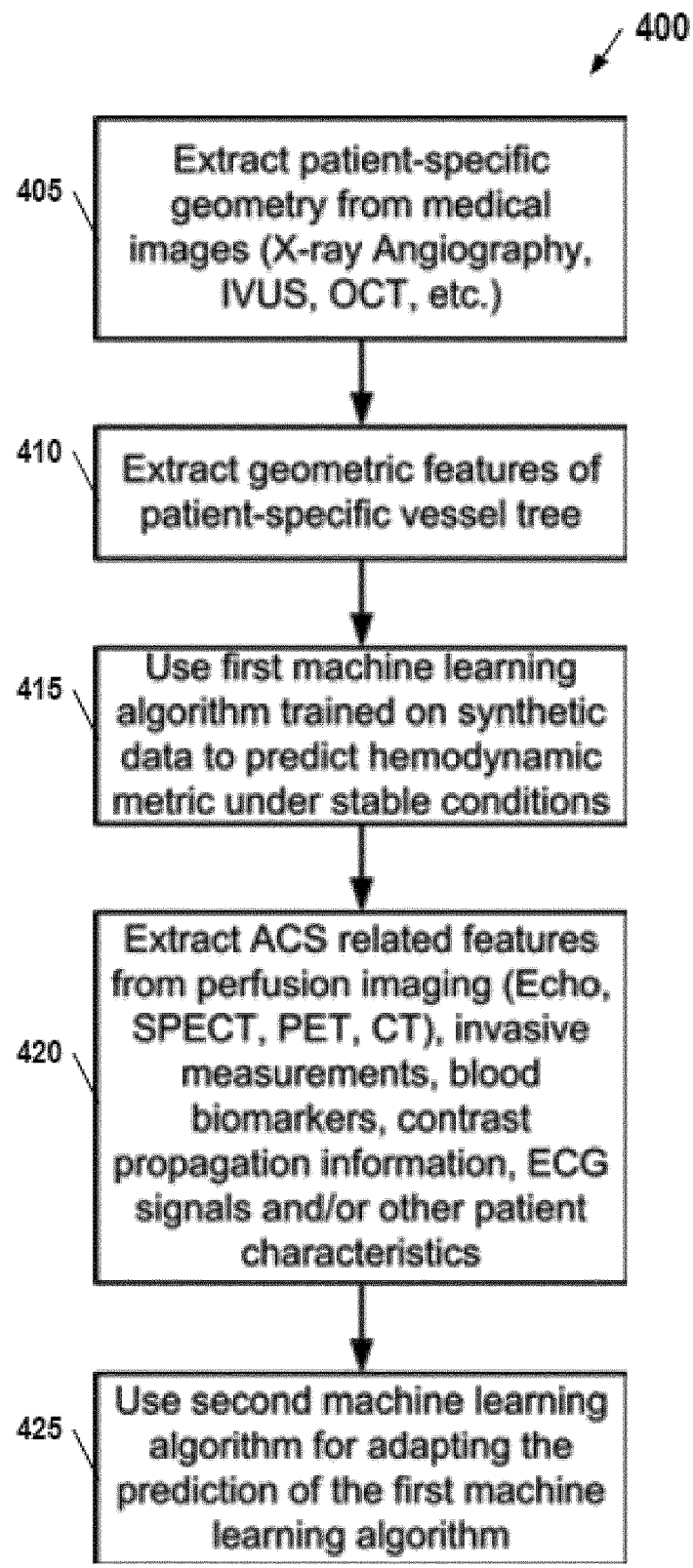
FIG. 4 illustrates a workflow used for the estimation of a quantity of interest in ACS patients from cascaded machine learning models, according to some embodiments.

FIG. 4 displays an example of the workflow 400 for the above described methodology. Starting at step 405, patient-specific geometry information is extracted from medical images. Next, at step 410, geometric features of the patient-specific vessel tree are extracted. Then, at step 415, a first machine learning algorithm trained purely on synthetic data is used to predict a hemodynamic metric such as stable ischemia under stable conditions.

Continuing with reference to FIG. 4, at step 420, ACS related features are extracted from patient characteristics. These characteristics may include, for example, measures of the infracted myocardial bed, as determined through perfusion imaging (Echo, SPECT, PET, CT); patient demographics (age, gender, BMI, height, mass, smoker/non-smoker, etc.); blood biomarkers (cTnT, cTnI, hs-cTnT, NT-proBNP, etc.); medication used in the past or present (aspirin, Beta-blocker, Nitrate, Statins, angiotensin converting enzyme inhibitors, Calcium-channel blockers, ARBs); or invasive pressure/flow measurements at any location of the coronary geometry ECG signals. Additionally (or alternatively), the features may include pathological history such as the presence of hypertension, presence of hyperlipidemia, diabetes mellitus, previous cardiovascular history (stroke, infarct, PCI, stent, CABG, etc.), non-invasive stress tests (e.g. stress echo), peripheral vascular disease, kidney disease, or exercise-based tests (e.g., exercise ECG, stress test, exercise radioisotope test, nuclear stress test, myocardial scintigraphy, etc.). Then, at step 425 a second ML algorithm uses the result predicted by the first algorithm at step 415 as feature, alongside the other patient characteristics and measures extracted at step 420, in order to obtain the final prediction, corresponding to the ACS conditions.

Figure 5:
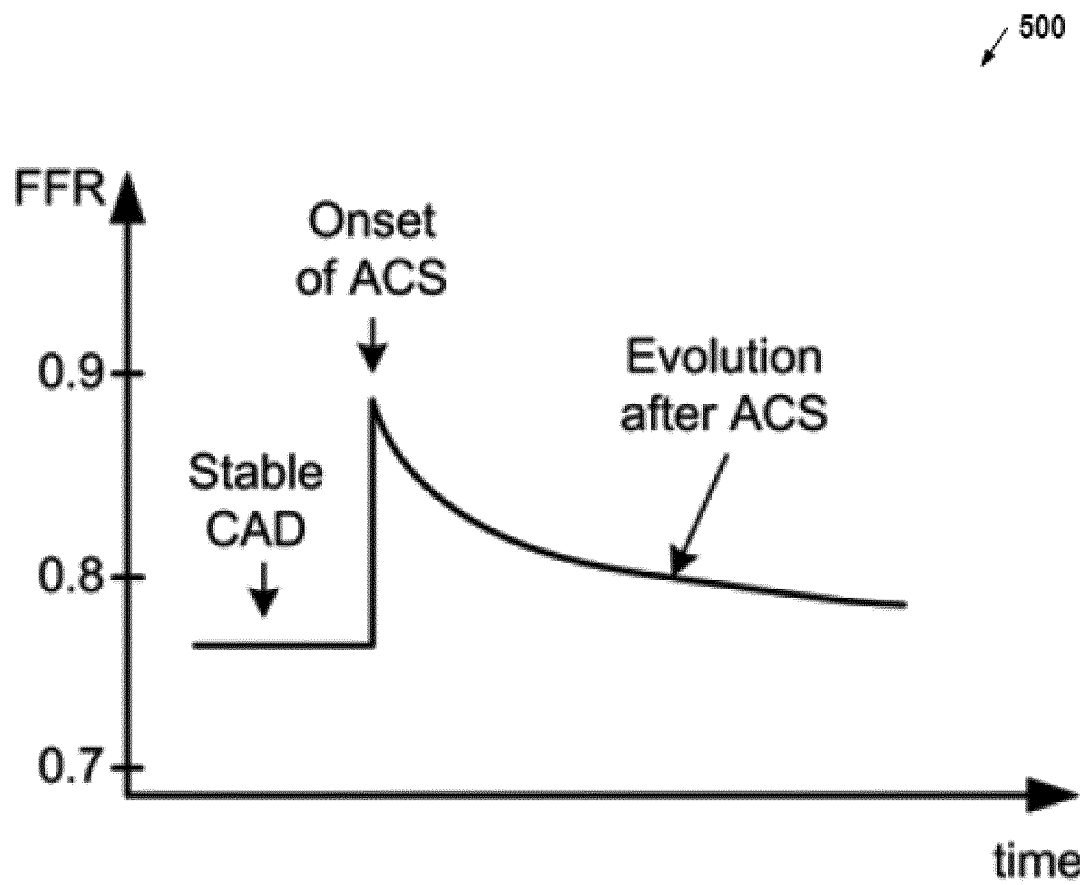
FIG. 5 provides an example of evolution in time of FFR before and after the onset of ACS.

Any of the above mentioned approaches may be used not only to predict a quantity of interest at a certain time point, but the evolution in time of the quantity of interest after the onset of ACS. FIG. 5 shows an example graph 500 illustrating FFR as quantity of interest. This evolution may correspond to both a culprit and a non-culprit artery (whose myocardial bed is affected by the ACS). As can be observed under conditions of stable CAS, the FFR value lies below the diagnostic threshold of 0.8. After the onset of ACS, the FFR value increases suddenly since the capability of achieving maximal hyperemia is impaired. The level of impairment then gradually decreases as time passes and the myocardial bed recovers. The myocardial bed may recover completely or not, depending on whether the myocardial bed of the artery of interest contains necrotic tissue or not.

A ML model may be trained to predict the curve describing the evolution of the quantity of interest after the onset of ACS. This curve may be parameterized (linear, logarithmic, exponential, etc.) and the ML model may predict parameter values corresponding to the evolution curve (e.g. time constant of the decay). Any of the features and methods described in the previous sections may be used during training and prediction.

Under conditions of ACS, multiple imaging modalities are often used to visualize coronary arteries including angiography to visualize all coronary arteries of interest and to determine the culprit artery or IVUS/OCT to visualize the artery of interest, i.e. to determine the plaque characteristics. In case such multiple images are available for the same artery they can be used to improve/extend the predictions of quantities of interest. The lumen boundary of an artery may be determined from coronary angiography and partially from OCT. Since OCT provides a more accurate estimation of the lumen, the OCT based lumen boundary may be used at locations where it is available.

By using a ML algorithm to predict the quantity of interest based on features whose value are determined either from the angiography or the OCT based lumen, additional measures of interest may be provided such as, for example, a confidence interval for the quantities of interest estimated from angiography or a measure of uncertainty for the quantities of interest estimated from angiography.

Additionally, by systematically analyzing the differences between the angiography based lumen and OCT based lumen, the angiography based lumen at locations where the OCT based lumen is not available may be corrected. This may provide better estimations for the quantities of interest at all locations of interest.

Figure 6:
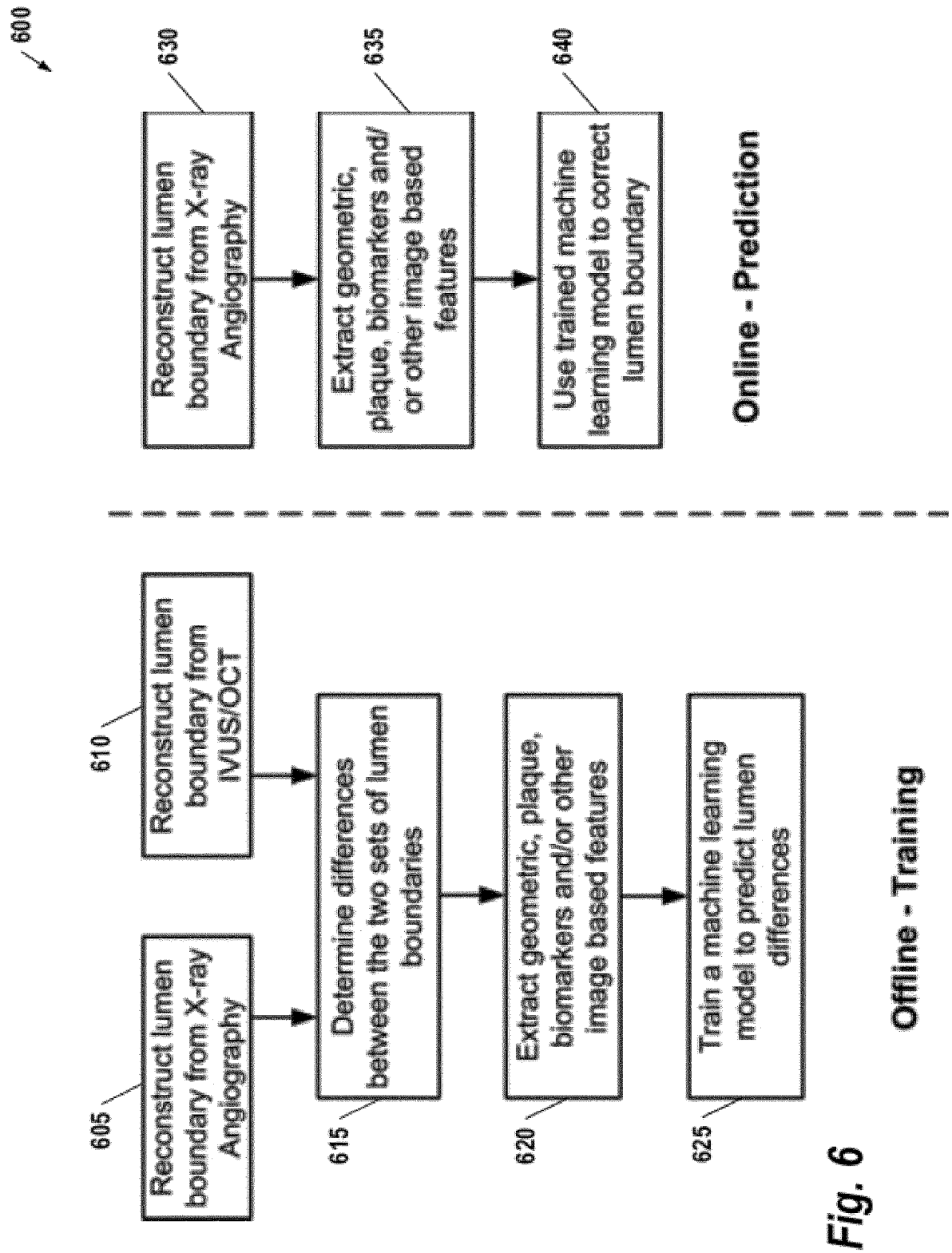
FIG. 6 shows a machine learning based workflow to correct lumen boundary, as may be applied in some embodiments.

FIG. 6 displays a workflow 600 which uses ML to correct the lumen boundaries. During the training phase, the angiography-based lumen and the lumen determined from intravascular imaging (IVUS/OCT) are determined at steps 605 and 610, respectively. The differences between the two lumen boundaries are then systematically determined at step 615. Next, at step 620 features related to these differences are extracted and, at step 625, a ML algorithm is trained to predict the differences based on the previously extracted features. During the prediction phase in the exaction, only the angiography based lumen is available. The lumen boundary is reconstructed from X-ray angiography at step 630. Various features are extracted at step 635 and used at step 640 to correct the lumen boundary using the previously trained ML algorithm. Several types of features may be used including geometric features such as stenosis shape, stenosis severity, orientation of vessel with respect to angiographic projection, bifurcation characteristics (stenosis, angle, etc.), etc. Additional examples of features that could be used include plaque characteristics (e.g. calcified plaque) or blood biomarkers. It should be noted that, although the workflow 600 show in FIG. 6 is used to correct the lumen, it may be readily adapted to correct other geometric characteristics determined through the different medical imaging techniques: radius/diameter/area of the vessel, length of the centerline, etc.

Another variation of the workflow 100 displayed in FIG. 1 refers to the prediction of a future cardiac event. A major cause for cardiac events is the rupture of coronary plaque, which may either block the large coronary arteries or block the microvasculature. Currently there is no model-based approach capable of fully explaining the formation, growth and rupture of the plaque. Several factors are linked to the risk of plaque rupture: anatomical characteristics of the plaque, anatomical characteristics of the arteries, hemodynamic measures (wall stress), composition of plaque, etc.

For example, coronary CT angiography may be used to characterize the morphology of the plaque (extent of remodeling, etc.) and determine its composition: lipid core, fibrous plaque, calcified plaque, necrotic plaque. Blood biomarkers have been shown to be linked to plaque characteristics. For example, C-reactive protein has been associated with certain coronary plaque subtypes (as imaged by Coronary Computed Tomography).

The arterial wall stress (e.g., shear stress, normal stress, total stress, cycle-averaged stress, instantaneous stress) may be used as a predictor of plaque rupture or in general as a predictor of a cardiac event. Wall stresses may be derived from pressure/flow measurements, computed by a blood flow model or predicted by a ML algorithm. In case of blood flow computations the material properties of the arterial wall, which are required for fluid structure interaction computations, may be derived from the plaque characteristics.

Furthermore, any other hemodynamic measure of interest computed by a blood flow model or predicted by a ML algorithm may be used to predict the risk of future events for ACS patients. The features used for the prediction may be non-invasive patient data (e.g., blood pressure, heart rate, demographics, patient history, etc.); non-invasive medical imaging (e.g., CT, Echocardiography, NIRS, etc.); invasive medical imaging (e.g., angiography, OCT, IVUS, etc.); perfusion imaging; blood biomarkers; invasive measurements (e.g., pressure, flow, etc.); hemodynamic measures of interest estimated from blood flow computations or predicted by other ML algorithms; myocardial jeopardy scores; and/or ECG signals. For example vascular echocardiography of femoral and carotid arteries may be used to evaluate arterial stiffness, intima/media thickness, etc.

The predicted risk may refer to plaque rupture (a separate risk score for each plaque or a combined score formulated by combining information from one or more plaques), re-infarction, cardiac failure, death, etc. The risk may be determined as a weighted sum of the risk score derived from each of the anatomical, morphological, hemodynamic and biochemical metrics (a composite risk score). Each of these individual scores can be computed by using the already established hypothesis for these respective factors from the clinical literature. If the risk is predicted by a ML algorithm, during the training phase, the algorithm is trained on a database containing multiple training examples together with ground truth. The training database can be populated in a number of different ways. For example, positive training examples can be the plaques that ruptured, and negative examples (from the same patient) are the plaques that did not rupture during an acute coronary syndrome event.

Figure 7:
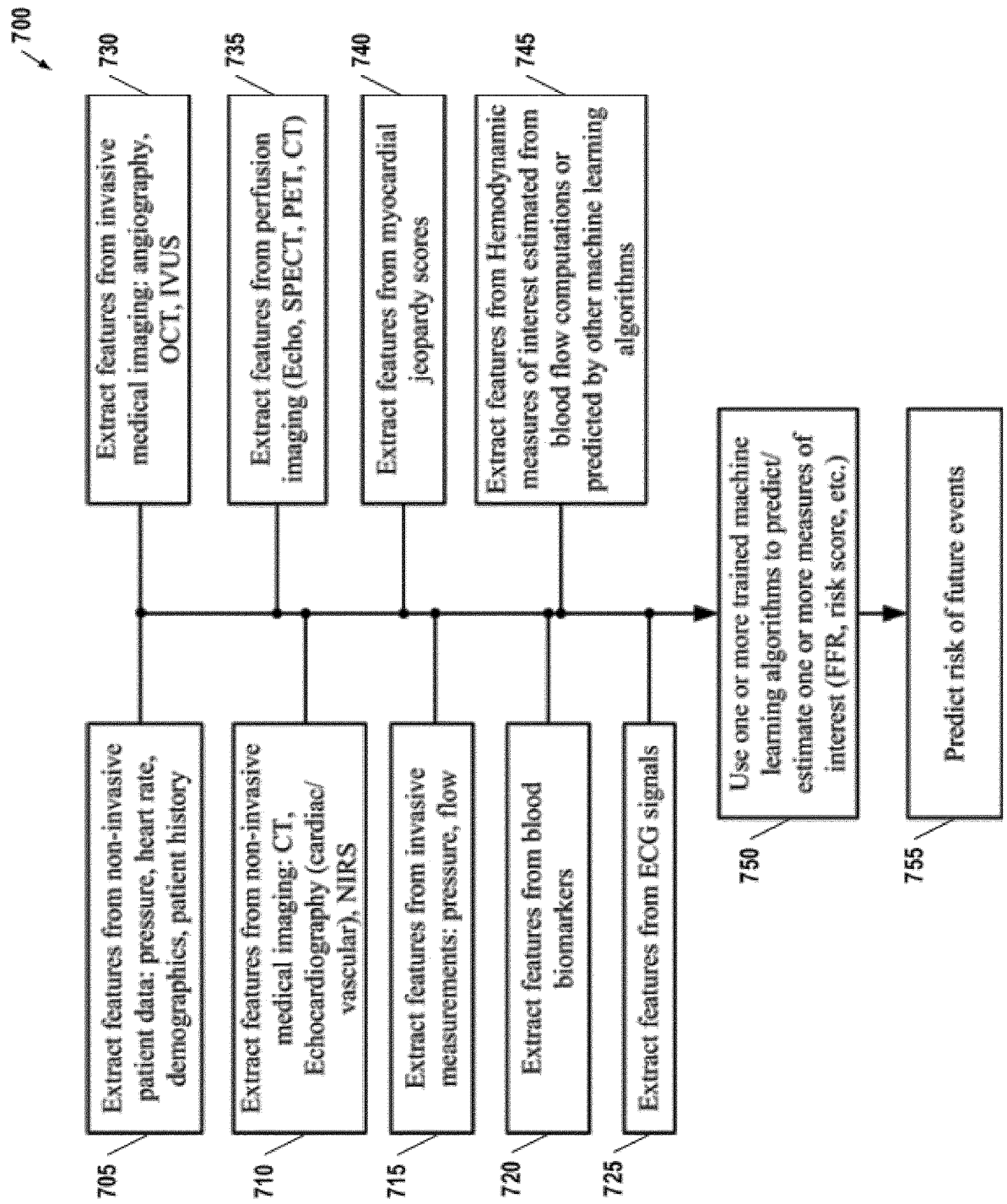
FIG. 7 illustrates a workflow used to predict risk of future events for patients with acute coronary syndrome, according to some embodiments.

FIG. 7 displays the corresponding workflow 700. Briefly, at steps 705-725 and step 730-745 various features are extracted from myriad data sources. Then, at step 750, one or more trained ML algorithms are used to predict/estimate one or more measures of interest. Then, the risk of future events is predicted at step 755 based on those measures of interest. It should be noted that the workflow 700 shown in FIG. 7 may also be used to predict other aspects of interest like the degree of recovery of the hyperemic response.

Any of the features and characteristics described above may be determined fully automatically, semi-automatically or manually by a user. In case of fully automatic extraction an algorithm determines the values of the characteristics. In case of semi-automated extraction an algorithm may propose an initial value which may then be corrected/edited by the user. In case of manual extraction, the user measures/determines the value of the characteristics. The above defined methods may also be used for therapy planning in ACS patients, i.e. ML algorithms may be used to indicate which stenosis to stent for an optimum outcome/minimum future risk of cardiac events, what type of medical therapy to prescribe, etc.

Figure 8:
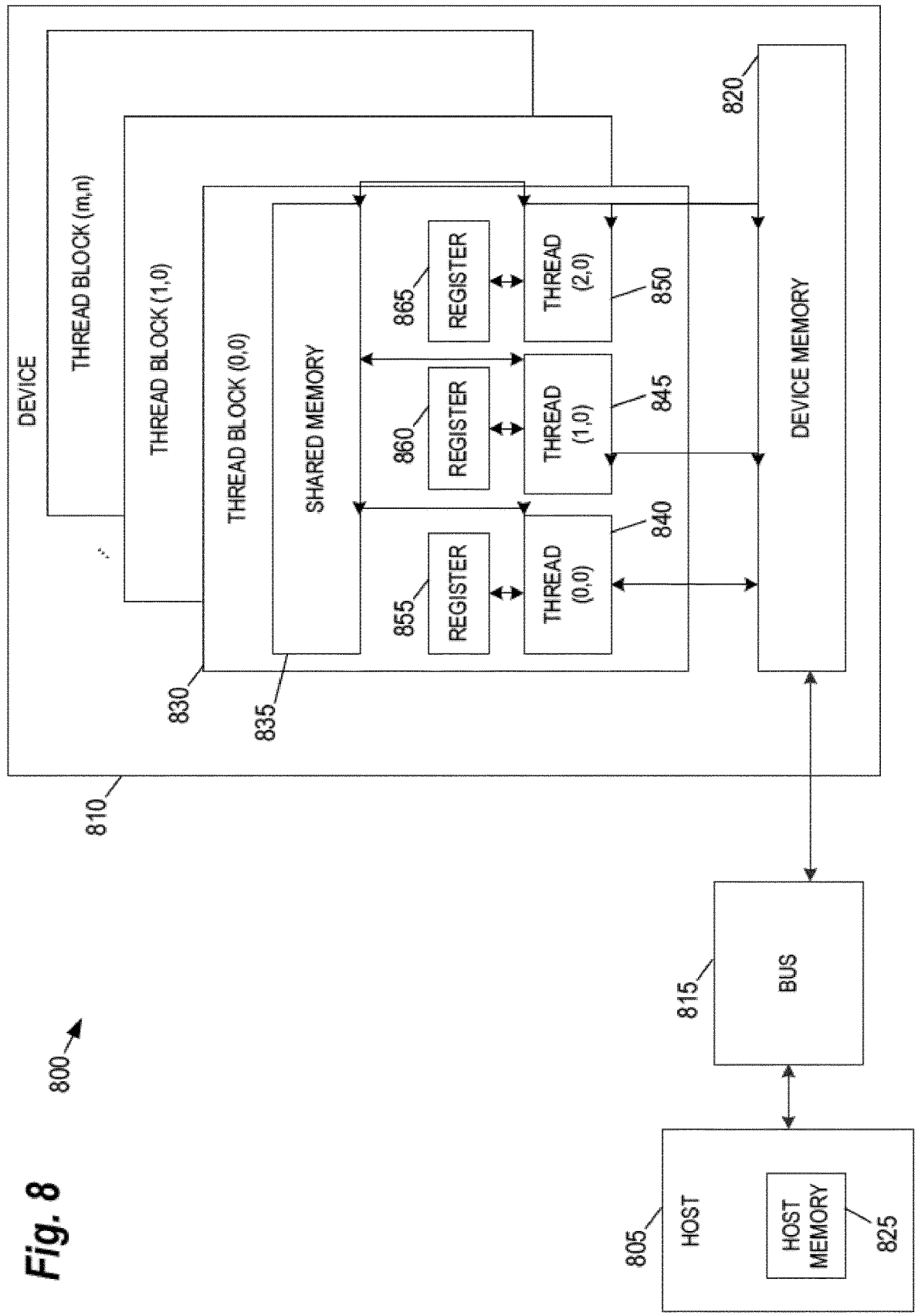
FIG. 8 provides an example of a parallel processing memory architecture that may be utilized to perform computations related to execution of the various workflows discussed herein, according to some embodiments of the present invention.

FIG. 8 provides an example of a parallel processing memory architecture 800 that may be utilized to perform computations related to execution of the various workflows discussed herein, according to some embodiments of the present invention. This architecture 800 may be used in embodiments of the present invention where NVIDIA™ CUDA (or a similar parallel computing platform) is used. The architecture includes a host computing unit ("host") 805 and a graphics processing unit (GPU) device ("device") 810 connected via a bus 815 (e.g., a PCIe bus). The host 805 includes the central processing unit, or "CPU" (not shown in FIG. 8), and host memory 825 accessible to the CPU. The device 810 includes the graphics processing unit (GPU) and its associated memory 820, referred to herein as device memory. The device memory 820 may include various types of memory, each optimized for different memory usages. For example, in some embodiments, the device memory includes global memory, constant memory, and texture memory.

Parallel portions of a deep learning application may be executed on the architecture 800 as "device kernels" or simply "kernels." A kernel comprises parameterized code configured to perform a particular function. The parallel computing platform is configured to execute these kernels in an optimal manner across the architecture 800 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 800 of FIG. 8 (or similar architectures) may be used to parallelize training of a deep neural network. For example, in some embodiments, the operations of the simulation platform may be partitioned such that multiple kernels execute simulate different configurations simultaneously (e.g., different viewpoints, lighting, textures, materials, effects, etc.). In other embodiments, the deep learning network itself may be implemented such that various operations performed with the training and use of the network are done in parallel.

The device 810 includes one or more thread blocks 830 which represent the computation unit of the device 810. The term thread block refers to a group of threads that can cooperate via shared memory and synchronize their execution to coordinate memory accesses. For example, in FIG. 8, threads 840, 845 and 850 operate in thread block 830 and access shared memory 835. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 8, the thread blocks 830 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. To address this limitation, workflow operations may be configured in various manners to optimize use of the parallel computing platform. For example, in some embodiments, various stages of feature extraction may be performed in parallel. Additionally (or alternatively), the ML algorithm used during the various prediction phases described herein may be selected and adapted based on the ability of the algorithms to be parallelized. Thus, for example, certain neural network algorithms may be preferable where operations associated with predictions of measures of interest can be performed in parallel.

Continuing with reference to FIG. 8, registers 855, 860, and 865 represent the fast memory available to thread block 830. Each register is only accessible by a single thread. Thus, for example, register 855 may only be accessed by thread 840. Conversely, shared memory is allocated per thread block, so all threads in the block have access to the same shared memory. Thus, shared memory 835 is designed to be accessed, in parallel, by each thread 840, 845, and 850 in thread block 830. Threads can access data in shared memory 835 loaded from device memory 820 by other threads within the same thread block (e.g., thread block 830). The device memory 820 is accessed by all blocks of the grid and may be implemented using, for example, Dynamic Random-Access Memory (DRAM).

Each thread can have one or more levels of memory access. For example, in the architecture 800 of FIG. 8, each thread may have three levels of memory access. First, each thread 840, 845, 850, can read and write to its corresponding registers 855, 860, and 865. Registers provide the fastest memory access to threads because there are no synchronization issues and the register is generally located close to a multiprocessor executing the thread. Second, each thread 840, 845, 850 in thread block 830, may read and write data to the shared memory 835 corresponding to that block 830. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 810 to read and/or write to the device memory. Device memory requires the longest time to access because access must be synchronized across the thread blocks operating on the device. Thus, in some embodiments, the processing of each seed point is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 8, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for personalized assessment of patients with acute coronary syndrome (ACS), the method comprising:
   extracting patient-specific coronary geometry data from one or more medical images of a patient;
   extracting a plurality of features of a patient-specific coronary arterial tree based on the patient-specific coronary geometry data, wherein the patient-specific coronary arterial tree is generated by estimating a total coronary resistance index ($TCRI_{ACS}$) value of each artery of the patient-specific coronary arterial tree; wherein each $TCRI_{ACS}$ is a function of a distance between a myocardial bed of each artery of the patient-specific coronary arterial tree and a myocardial area affected by the ACS;

extracting a plurality of ACS-related features from additional patient measurement data including blood biomarkers acquired at different time points and contrast propagation information; and using a surrogate model to predict patient-specific hemodynamic measures of interest related to ACS based on the plurality of features of the patient-specific coronary arterial tree and the plurality of ACS-related features from the additional patient measurement data.

2. The method of claim 1, wherein the additional patient measurement data further comprises one or more of perfusion imaging data, invasive measurements, and ECG signals.

3. The method of claim 1, wherein the patient-specific hemodynamic measures of interest comprise one or more of Fractional Flow Reserve and Coronary Flow Reserve.

4. The method of claim 1, wherein the patient-specific hemodynamic measures of interest comprise wall shear stress.

5. The method of claim 1, wherein the patient-specific hemodynamic measures of interest comprise risk of plaque rupture.

6. The method of claim 1, further comprising training the surrogate model using a process comprising:

generating a database of coronary arterial trees representative of ACS conditions;

performing flow computations on each artery included in the database of coronary arterial trees to extract hemodynamic measures of interest;

extracting features of coronary arterial trees and ACS related features from the database of coronary arterial trees;

applying one or more machine learning methods to train the surrogate model to predict the hemodynamic measures of interest based on the features of coronary arterial trees and the ACS related features.

7. The method of claim 6, wherein the database of coronary arterial trees comprises a plurality of synthetic coronary arterial trees.

8. The method of claim 7, wherein the database of coronary arterial trees comprises a plurality of in silico models and the flow computations comprise computational fluid dynamics (CFD) computations.

9. The method of claim 7, wherein the database of coronary arterial trees comprises a plurality of in vitro models and the flow computations comprise flow experiments.

10. The method of claim 7, wherein the database of coronary arterial trees further comprises a plurality of non-synthetic coronary arterial trees.

11. The method of claim 1, further comprising:

predicting a risk of future events for patients with ACS based on the patient-specific hemodynamic measures of interest.

12. The method of claim 1, further comprising:

determining a confidence interval or a measure of uncertainty for the patient-specific hemodynamic measures of interest related to ACS.

13. The method of claim 12, wherein the confidence interval or the measure of uncertainty is determined by comparing the predictions of the surrogate model based on medical images of the patient-specific coronary geometry acquired with at least two different imaging modalities.

14. A computer-implemented method for personalized assessment of patients with acute coronary syndrome (ACS), the method comprising:

extracting patient-specific coronary geometry data from a plurality of medical images;

extracting geometric features of a patient-specific vessel tree based on the patient-specific coronary geometry data;

training a first machine learning model on a database of synthetic coronary arterial trees; wherein the database of synthetic coronary arterial trees representative of ACS conditions are generated by estimating a total coronary resistance index ($TCRI_{ACS}$) value of each artery of each synthetic coronary arterial tree; wherein each $TCRI_{ACS}$ is a function of a distance between a myocardial bed of each artery of each synthetic coronary arterial tree and a myocardial area affected by the ACS;

using the first machine learning model to determine one or more patient-specific hemodynamic measures of interest under stable conditions based on the patient-specific vessel tree;

extracting a plurality of ACS-related features from additional patient measurement data including blood biomarkers acquired at different time points and contrast propagation information; and using a second machine learning model to refine the one or more patient-specific hemodynamic measures of interest based on the plurality of ACS-related features.

15. The method of claim 14, wherein the additional patient measurement data further comprises one or more of perfusion imaging data, invasive measurements, and ECG signals.

16. The method of claim 14, wherein the one or more patient-specific hemodynamic measures of interest comprise one or more of Fractional Flow Reserve and Coronary Flow Reserve.

17. The method of claim 14, wherein the one or more patient-specific hemodynamic measures of interest comprise wall shear stress.

18. The method of claim 14, wherein the one or more patient-specific hemodynamic measures of interest comprise risk of plaque rupture.

19. The method of claim 14, further comprising:

predicting a risk of future events for patients with ACS based on the one or more patient-specific hemodynamic measures of interest.

20. The method of claim 14, further comprising:

predicting evolution in time of the hemodynamic measures of interest after onset of ACS.

21. A parallel processing computing system for personalized assessment of patients with acute coronary syndrome (ACS), comprising:

a host computer configured to:

extract patient-specific coronary geometry data from one or more medical images of a patient, extract features of a patient-specific coronary arterial tree based on the patient-specific coronary geometry data, wherein the patient-specific coronary arterial tree representative of a ACS condition is generated by estimating a total coronary resistance index ($TCRI_{ACS}$) value of each artery of the patient-specific coronary arterial tree; wherein each $TCRI_{ACS}$ is a function of a distance between a myocardial bed of each artery of the patient-specific coronary arterial tree and a myocardial area affected by the ACS, and extract a plurality of ACS-related features from additional patient measurement data including blood biomarkers acquired at different time points and contrast propagation information; and a device computer configured to predict patient-specific hemodynamic measures of interest related to ACS based on the features of the patient-specific coronary arterial tree and the plurality of AC S-related features from the additional patient measurement data by applying one or more machine learning models in parallel across a plurality of computation units.

\* \* \* \* \*